United States Patent [19]

Achterholt

[11] Patent Number: 5,718,687

[45] Date of Patent: Feb. 17, 1998

[54] EXTRA-CORPORAL BLOOD PUMP

[75] Inventor: Rainer Achterholt, Durach/Weidach, Germany

[73] Assignee: Deco Delta GmbH, Stuttgart, Germany

[21] Appl. No.: 708,776

[22] Filed: Sep. 5, 1996

[30] Foreign Application Priority Data

Sep. 11, 1995 [DE] Germany ............ 195 33 595.3

[51] Int. Cl.$^6$ .................................................. A61M 37/00
[52] U.S. Cl. ........................ 604/131; 604/133; 604/153; 604/4; 128/DIG. 12
[58] Field of Search ...................... 604/4, 5, 6, 131, 604/132, 133, 151, 152, 153, 154, 155, 156, 319, 321; 128/DIG. 12

[56] References Cited

U.S. PATENT DOCUMENTS

| 500,739 | 3/1893 | Kulisz et al. | 604/132 |
|---|---|---|---|
| 3,513,486 | 5/1970 | de Bennetot et al. | 3/1 |
| 3,582,234 | 6/1971 | Isreeli | 604/153 X |
| 3,884,228 | 5/1975 | Hahn | 604/131 |
| 4,076,467 | 2/1978 | Persson | 417/478 |
| 4,460,354 | 7/1984 | Weilbacher et al. | 604/131 X |
| 4,634,430 | 1/1987 | Polaschegg | 604/141 |
| 4,642,088 | 2/1987 | Gunter | 604/4 |
| 4,798,578 | 1/1989 | Ranford | 604/4 |
| 4,857,042 | 8/1989 | Schneider | 604/4 |
| 4,981,473 | 1/1991 | Rosenblatt | 604/133 |

FOREIGN PATENT DOCUMENTS

| 2 299 532 | 1/1976 | France . |
|---|---|---|
| 1 504 494 | 5/1996 | France . |
| 657 670 A5 | 9/1986 | Switzerland . |

Primary Examiner—Sam Rimell
Assistant Examiner—Robert V. Racunas
Attorney, Agent, or Firm—Pollock, Vande Sande & Priddy

[57] ABSTRACT

An extra-corporal blood pump comprises a support means equipped with a pumping means and a driving means. Said pumping means comprises an inlet head, an outlet head and a pump chamber arranged between and connecting said inlet head with said outlet head, wherein:

said inlet head is stationarily arranged at said support means and comprises an inlet connector, an inlet bore having an internal diameter, and an inlet valve means;

said outlet head is movably arranged to be displaced by said driving means and comprises an outlet connector, an outlet bore having an internal diameter and an outlet valve means;

said pump chamber comprises a piece of a hose having a given original length and made of a rubber-elastic material and defining an interior volume of said pump chamber, wherein said piece of hose comprises an inlet end tightly connected with said inlet head, and further comprises a distantly arranged outlet end tightly connected with said outlet head; and said driving means periodically moving forward said outlet head essentially in a length direction of said hose piece thus streching the hose piece in order to increase per stroke the original hose piece length by at least 100% and by not more than about 500% of the original hose piece length without substantially narrowing the interior volume of the pump chamber, thus providing an enforced blood flow from the inlet bore through the pump chamber to the outlet bore.

16 Claims, 3 Drawing Sheets

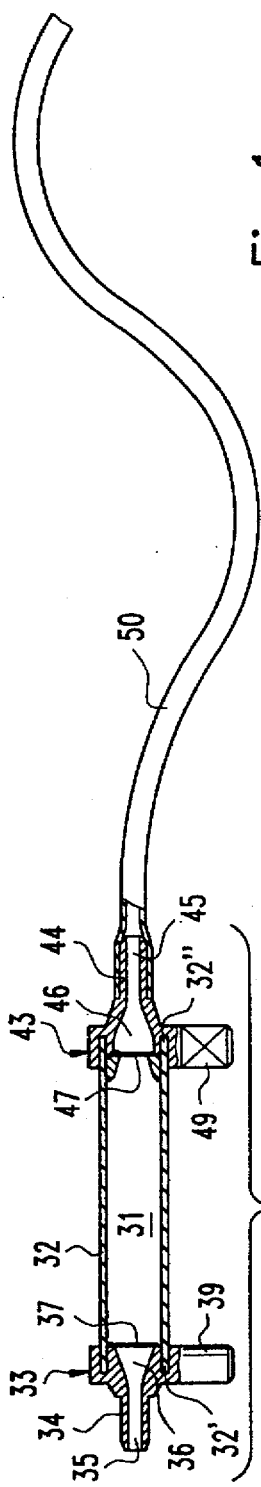
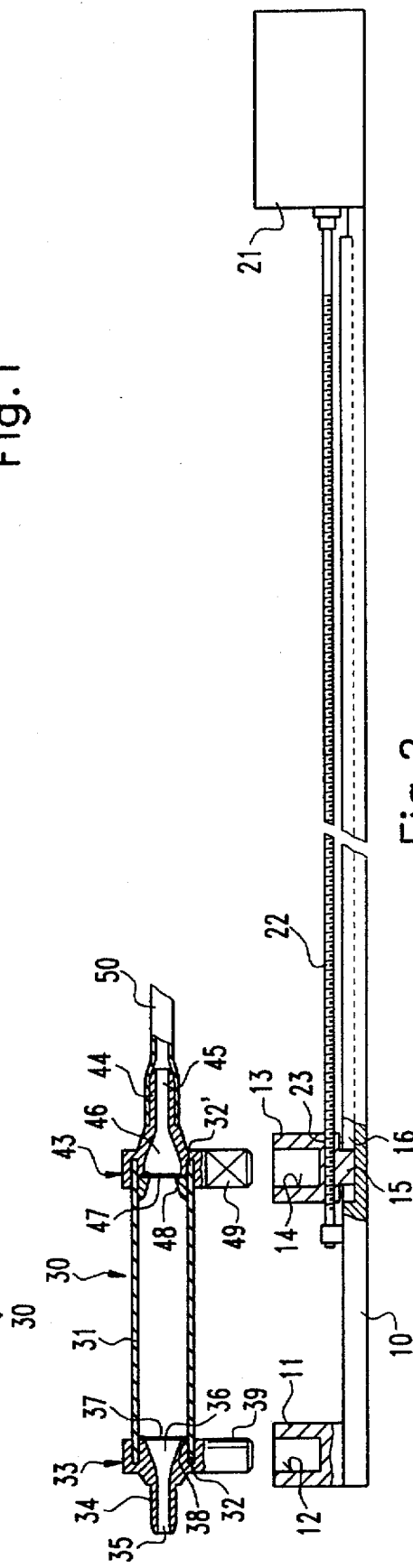
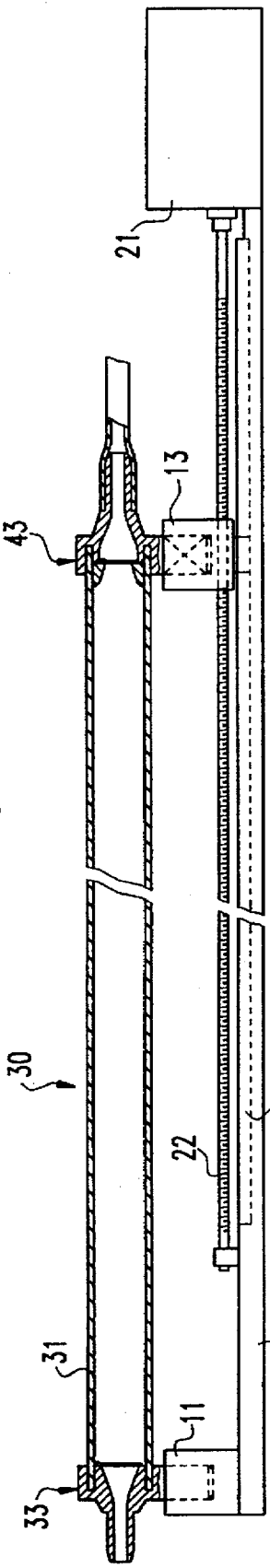
Fig.1
Fig.2
Fig.3

EXTRA-CORPORAL BLOOD PUMP

SPECIFICATION

The present invention is related to an extra-corporal blood pump comprising a support means equipped with a pumping means and a driving means, wherein said pumping means comprises an inlet head, an outlet head and a pump chamber arranged between and connecting said inlet head with said outlet head, and said driving means periodically moving forward said outlet head. Especially, an extra-corporal blood pump according to the present invention is intended for transportation of blood through a dialyzer. Typically, a dialyzer comprises a blood flow rate of about 100 ml/min; in specific cases, a blood flow rate up to about 250 ml/min may be provided.

An extra-corporal blood pump of the present type is known from document EP-A1-0 418 208. The known blood pump comprises each a movable arrangement of the inlet head and of the outlet head in order to move said heads periodically towards each other and away from each other, whereby an interior volume of the pump chamber being variable in accordance with the relative distance between the inlet head and the outlet head. The known pump chamber is constructed as a substantially spherical bladder having flexible but substantially non-stretchable walls and which is constructed in such a manner as to enable a part of its wall to be folded telescopically from the spherical state to a folded state when both the inlet head and the outlet head are moving towards together. In this way the interior volume of the pump bladder or of the pump chamber varies in accordance with the varying distance between the inlet head and the outlet head. Due to the specific movable arrangement of these heads, no sub-pressure can be generated at the pump inlet or in the pump itself and neither any unpermissible overpressure at the pump outlet or in the pump itself. The known blood pump shall be designed and constructed in such a manner that no mechanical damages will occur to the blood corpuscles in the pumped blood.

The document EP-A1-0 659 444 discloses a device for pumping blood, said device comprises a pulsating bladder being periodically compressed and expanded by external pressure variations and thus transporting blood in a pulsating manner. Said known bladder is arranged within a rigid pressure-tight housing, and a pressurized fluid is fed by means of a pump into said housing in order to periodically compress and expand said bladder. Said known blood pump does not comprise a movably arranged outlet head. Because said known bladder is arranged within a pressure-tight housing it is not easy to remove and replace said known bladder by a fresh bladder.

The document EP-A1-0 478 499 discloses an intermittently transporting blood pump comprising a movably arranged push body acting on a deformable pressure-tight bladder. An electric hollow shaft motor is used to move said push body; in detail, said motor drives a threaded spindle engaging a nut coupled with said push body, thus providing a linear driving force in order to move said push body.

The classical and widely used pump for transporting blood through a dialyzer comprises the peristaltic roller pump comprising two or three rolls which revolve along a circle path and thus compress a squeezable hose arranged along said circle path. Each roll squeezes the pressure hose to such an extent that the hose inner wall sections engage each other and close the hose cross section. The continuous revolving of the rolls along the circle path transports the blood column arranged in front of each squeezing spot through the interior volume of the hose. A "peristaltic" roller pump of said type provides several advantages. The pumping means consisting of an inlet head, said squeezable hose and an outlet head forms a simple and low cost component which may be easily inserted into a pump device and which may be easily removed and replaced by a fresh pumping means subsequently to a single use of the original pumping means. Besides the squeezing spots there are no substantial modifications of the cross section of the blood column within said hose; therefore, substantial shearing stresses, turbulent flow areas and dead-water areas within the blood column are avoided. On the other hand, the possibility of deformations, deteriorations and damages of the living blood cells, such as erythrocytes, echinocytes, spherocytes and stomatocytes may occur in the region of the squeezing spots. Said deformations and deteriorations of the living blood cells may cause a hemolysis.

Consequently, the peristaltic roller pump has the serious drawback that it is very difficult to avoid considerable damages to the blood corpuscles in the pumped blood in consequence of the squeeze and shear forces that the blood corpuscles are subjected too within the pump.

Accordingly, it is an object of the present invention to provide a blood pump comprising an inlet head, an outlet head, a pump chamber arranged between and connecting said inlet head with said outlet head, and a driving means for moving said outlet head, wherein said blood pump still maintains the advantageful properties of a peristaltic roller pump but avoiding the drawbacks which are especially caused by the squeezing of the hose of the peristaltic roller pump.

The present invention provides an extracorporal blood pump, especially for transportation of blood through a dialyzer, said blood pump comprising a support means equipped with a pumping means and a driving means, wherein said pumping means comprises an inlet head, an outlet head and a pump chamber arranged between and connecting said inlet head with said outlet head, wherein:

said inlet head is stationarily arranged at said support means and comprises an inlet connector, an inlet bore having an internal diameter, and an inlet valve means;

said outlet head is movably arranged to be displaced by said driving means and comprises an outlet connector, an outlet bore having an internal diameter and an outlet valve means;

said pump chamber comprises a piece of a hose having a given original length and made of a rubber-elastic material and defining an interior volume of said pump chamber, wherein said piece of hose comprises an inlet end tightly connected with said inlet head, and further comprises a distantly arranged outlet end tightly connected with said outlet head; and said driving means periodically moving forward said outlet head essentially in a length direction of said hose piece thus streching the hose piece in order to increase per stroke the original hose piece length by at least 100% and by not more than about 500% of the original hose piece length without substantially narrowing the interior volume of the pump chamber, thus providing an enforced blood flow from the inlet bore through the pump chamber to the outlet bore.

Preferably, said periodical movement of said outlet head will increase per stroke the original hose piece length by at least 100% and by not more than about 400% of said original hose piece length without substantially narrowing the interior volume of the pump chamber.

According to a preferred aspect, said piece of hose defines an interior volume of said pump chamber having an internal diameter not larger than five-times the internal diameter of the inlet bore of said inlet head and/ or of the outlet bore of said outlet head.

According to another preferred aspect, said given original length of the non-stretched hose piece or of the pump chamber, respectively, is larger than said internal diameter of said pump chamber/non-stretched hose piece.

The blood pump according to the present invention comprises a pumping unit or pumping means consisting of said inlet head, of said pump chamber, and of said outlet head. The fore-mentioned geometric features provide a pumping means which avoids substantial differences between at one hand the internal diameter of the stretchable hose piece and on the other hand of the internal diameter of the inlet bore and/or of the internal diameter of the outlet bore. In addition, the inlet valve means and/or the outlet valve means avoid substantial modifications and/or restrictions of the blood column. Any transitions from the inlet bore through the inlet valve means into the hose piece and from the hose piece/pump chamber through the outlet valve means and the outlet bore are formed smooth with an easy continuous gradient in order to avoid any turbulent flow of the pumped blood.

The present invention provides a simply constructed blood pump comprising a hose-like blood chamber which does no longer require squeezing and reduction of the internal diameter of said hose in order to transport blood. The fore-mentioned geometric features and the smooth transitions between the bores and passages of the several components avoid substantial shearing stresses, turbulent flow areas and dead-water areas of the pumped blood within the pumping means.

Said pumping means according to the present invention comprises a simple constructed and low cost unit intended for easy and independent handling which may be easily inserted into a pump support and easily removed from said pump support and replaced against a new or fresh pumping means of the same or similar kind. Insofar, said pumping means represents a low cost disposable article intended for a single use.

The blood pump according to the present invention avoids the serious drawbacks but maintains the advantages of the peristaltic roller pump.

According to a preferred embodiment of the present invention, said outlet head is reciprocally moving forward and backward essentially in the length direction of said hose piece, wherein said periodically moving forward being provided by said driving means, and said periodically moving backward being provided by an inherent elastic restoring force of the hose material of the stretched hose piece. Periodically moving forward said outlet head stretches the hose piece, thus increasing the interior volume of the pump chamber and creating a suction action within the pump chamber. Preferably, the inlet valve means comprises a check valve, for example a flap or membrane valve, and allowing under said suction action a blood flow from a supply line connected to said inlet connector through said inlet bore into the pump chamber. Further, and according to a preferred embodiment, the outlet means comprises a check valve, for example a flap or membrane valve, which closes the outlet bore under said suction action.

Periodically moving backward said outlet head reduces the stretched length of the hose piece to its original length, thus decreasing the interior volume and creating a pumping action within the pump chamber. Under said pumping action, the inlet valve means closes the inlet bore.

Further, said pumping action enables the outlet valve means to open the outlet bore thus creating a blood flow out of the pump chamber through the outlet bore into a dispensing line connected to the outlet connector.

According to a further preferred embodiment of the present invention the stretchable hose piece is consisting of a rubber-elastic material suited for medium purposes; suited materials include rubber-elastic silicon materials, polyurethane materials and latex materials. Especially, a latex foil comprising a thickness of about 0.4 mm may be stretched to increase its original length by at least 600% and provides a sufficient durability to endure at least several thousand strokes. Rubber-elastic materials of said type are known in the medical field, for example for the manufacturing of medical gloves, and are available commercially.

According to a further preferred embodiment, the blood pump according to the present invention comprises an elongated support means having a stationary fastening means arranged adjacent to an end portion of said support means and enabled to fasten the inlet head of the pumping means. Said fastening means may comprise a stationarily arranged and extending cylindrical bolt, and the inlet head may comprise an adapted bore in order to push said inlet head on said bolt such that said bolt will extend through said bore in order to provide a stationary but swinging or tilting arrangement of the inlet head at said bolt. Another type of stationary fastening means may comprise a retaining means such as a hole, and the inlet head may comprise an adapted fastening extension insertable into said hole. Said hole may comprise a specific internal contour, for example a cylindric contour, and the fastening extension of the inlet head may comprise an adapted external contour, in order to insert only the fastening extension of said inlet head into the stationarily arranged retaining means.

Further, said support means of the blood pump is additionally comprising a movably arranged fastening means enabled to fasten said outlet head. Said movably arranged fastening means is moved or driven by a driving means in order to periodically stretch the hose piece forming the pump chamber. For example, said movably arranged fastening means may be guided along a groove or guidance extending in a length direction of said support means, and the driving means may comprise an electric step motor driving a threaded spindle which engages a nut or a threaded portion coupled to said movably arranged fastening means holding the outlet head. In this case, the movably arranged fastening means may comprise a retaining means such as a hole having a specific internal contour, for example a polygonal profile allowing only the insertion of a specific fastening extension of the outlet head having an adapted external contour, such as a polygonal post.

According to another example, the driving means may comprise a motor-driven rotating disc having a vertically extending peripheral link or may comprise a motor driven crank bolt having a vertically extending peripheral link, both peripheral links are enabled to revolve along a circle path. Said outlet head may comprise an adapted bore allowing to push said outlet head on said peripheral link such that said revolving peripheral link will cause a periodical stretching and shortening of said hose piece forming the pump chamber.

According to a still further embodiment, the driving means may comprise a motor-driven toothed wheel simultaneously driving a first driven gear wheel and a second driven gear wheel arranged distantly to each other and both matching with said driving toothed wheel. Each driven gear wheel comprises a vertically extending peripheral link, for example a vertical extending pin or bolt. In this specific case, the blood pump comprises a first pumping means having a first inlet head, a first pump chamber and a first outlet head, and further comprises a second pumping means having a second inlet head, a second pump chamber and a second outlet head. The first outlet head is coupled to the peripheral link of the first driven gear wheel, and the second outlet head is coupled to the peripheral link of said second driven gear wheel, thus simultaneously operating said first pumping means and said second pumping means.

Especially in connection with a driving means comprising a revolving peripheral link causing both, the stretching and the shortening of the hose piece, it might be helpful to provide a kind of cage means hindering a rather thin hose piece from an undue bulging or bagging during the shortening step, generating at least a slight overpressure within the pump chamber in order to press the blood into the dispensing line. Said cage means may comprise a rigid, cylindric casing or envelope formed integrally (in a one-piece manner) with the inlet head. Said casing or envelope comprises an inner diameter being a little bit larger than the outer diameter of the non-stretched hose piece.

In the following the invention will be explained in more detail referring to preferred embodiments as depicted in the drawings; said drawings merely serve for explanation purposes and may not be construed to limit the scope of the invention; in said drawings FIG. 1 shows a diagrammatic side view of a pumping means including an inlet head, a pump chamber and an outlet head;

FIG. 2 shows a diagrammatic side view of a blood pump, wherein the movably arranged outlet head takes a position just before stretching the hose piece in order to fill the pump chamber with additional blood;

FIG. 3 shows a similar diagrammatic side view like FIG. 2, however, wherein the movably arranged outlet head takes the position subsequently to the stretching action and just before the shortening of the hose piece in order to press blood into a dispensing line;

Figure 4A:
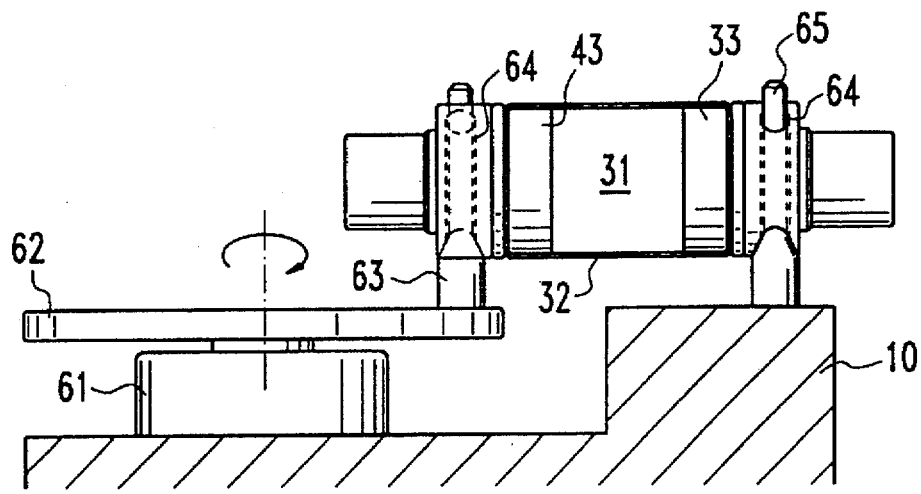
FIG. 4a shows a diagrammatic side view of a blood pump comprising another kind of a driving means wherein a revolving link, vertically extending from a peripheral section of a rotating disc will periodically stretch and shorten the hose piece.

A blood pump according to the present invention comprises essentially three main components, that is a support means 10, a pumping unit or pumping means 30 forming an independent, easily replaceable structural component, and a driving means.

Said pumping means 30 comprises a piece of a stretchable hose 32, an inlet head 33 and an outlet head 43. The stretchable hose piece 32 defines a pump chamber 31 and is made of a rubber-elastic material suited for medical purposes. Said rubber-elastic material may be stretched or extended to at least 400%, preferably to about 500% of its original length without substantially constricting an interior volume of the pump chamber 31. A suited and preferred material is a natural latex material having a thickness of about 0.4 mm. An undue constriction of the interior volume of the pump chamber 31 during the stretching step of the hose piece 32 may be avoided by a relatively large diameter of the hose piece 32, by a selected wall thickness of the hose piece 32 and/or by a selected shore hardness of the hose piece material. The hose piece material shall be inert with respect to blood and may not release or emit components such as softening agents into the blood. Preferably, the hose surface is even and comprises biocompatible properties. Suited rubber-like hose materials include silicone rubber, selected polyurethanes and natural latex materials. The hose piece may comprise an internal diameter of from about 4 mm to about 25 mm. In order to transport blood through an oxigenator, a hose diameter until about 12 mm (half-inch hose) is preferred. Even more preferred is a hose diameter of from about 4 mm to about 8 mm, in order to keep the differences between the hose diameter and the bores of the inlet head and/or the outlet head as small as possible.

The non-extended pump chamber 31 shall comprise a length of several cm, in order to avoid any contact between the inner front faces of the inlet head and the outlet head and to provide even in the non-stretched condition a certain blood volume which helps to minimize a turbulent blood flow within the blood chamber 31. In order to increase the volume of transported blood per stroke, it is more preferred to increase the length of the blood chamber 31 than to increase the internal diameter of said blood chamber 31.

The hose piece 32 comprises two distant hose ends 32' and 32". The one hose end 32' is connected safe and tightly with the inlet head 33, and the other hose end 32" is connected safe and tightly with the outlet head 43. Each head 33, 43 may comprise an injection molded article made of a biocompatible plastic material such as polycarbonate, polyethylene, polypropylene or polyurethane. If desired, the blood contacted surface sections may additionally comprise a coating of a biocompatible carbon material. The inlet head 33 comprises an inlet connector 34 and further defines an inlet bore 35. Typically, the inlet connector 34 may be connected to a—non-depicted—supply line which may be connected with a needle to be inserted in a patient's artery or may be connected with a container for intermediate storing of blood which has been tapped from a patient. The diameter of the inlet bore 35 corresponds with the diameter of the supply line. Preferably, the internal bore 35 may comprise a rather large internal diameter in order to keep the difference to the internal diameter of the pump chamber 31 as low as possible. Within the inlet head 33 the internal diameter of the inlet bore 35 may enlarge towards the pump chamber 31 in order to provide a bell-mouth enlargement 36.

An inlet valve means 37 is arranged adjacent to the inlet bore 35 or adjacent to the enlargement 36 of said inlet bore 35. The purpose of said inlet valve means 37 is to provide a blood flow from the supply line through the inlet bore 35 into the pump chamber 31 in case of a sub-pressure condition (caused by stretching the hose piece 32) within the pump chamber 31, and to close the inlet bore 35 in case of a overpressure condition (caused by a shortening of the hose piece 32) within the pump chamber 31. These functions may be performed by a simple check valve comprising a movably arranged valve means, such as a flap, flag, sail or membrane 37, resting with at least a part of its circumferential edge section on a supporting surface 38 formed at the inlet head 33 and serving as valve seat face.

Further, the pumping means 30 comprises an outlet head 43 having an outlet connector 44, an outlet bore 43 provided with an enlargement 46 towards the pump chamber 31, and an outlet valve means 47. In general, the structure and function of said outlet head 43 is similar to the above explained structure and function of the inlet head 33. The purpose of the outlet valve means 47 is to close the outlet bore 45 whenever a sub-pressure condition occurs within the pump chamber 31, and to allow a blood flow out of the pump chamber 31 through the outlet bore 45 into a dispensing line 50 whenever a overpressure condition occurs within the pump chamber 31. An elongated flexible dispensing line 50 may be connected to the outlet connector 44; said dispensing line 50 may lead to a—non-depicted—dialyzer or to another apparatus of an extracorporal blood circulation system.

The outlet bore 45 may comprise an internal diameter similar to the internal diameter of the inlet bore 35. Preferably, both, the inlet bore 35 and the outlet bore 45 may comprise an internal diameter of from about 1 mm to about 6 mm, even more preferred an internal diameter of from about 2 mm to about 5 mm and most preferred an internal diameter of from about 2 mm to about 4 mm. According to a preferred an important aspect of the present invention the internal diameter of the pump chamber 31, this means of the non-stretched hose piece 32 shall not be larger than five-times the internal diameter of the inlet bore 35 and/or of the out-let bore 45. This feature ensures a gentle and essentially non-turbulent blood flow from the inlet connector 34 through the pump chamber 31 to the outlet connector 44 minimizing any deterioration or damage of the living blood corpuscles. In so far, this feature ensures the function of the blood pump according to the present invention; this blood pump is characterized by a most simple structure.

The purpose of the outlet valve means 47 is to ensure a blood flow out of the pump chamber 31 through the outlet bore 45 into the dispensing line 50 whenever an overpressure condition with respect to the atmospheric pressure in the neighbourhood occurs, and to close the outlet bore 45, whenever a sub-pressure condition occurs within the pump chamber 31, thus avoiding a backward flow of the blood column out of the dispensing line 50 into the pump chamber 31. A cooperation of the inlet valve means 37 with the outlet valve means 47 allows only a blood flow in the direction from the inlet connector 34 through the pump chamber 31, through the outlet connector 44 and into the dispensing line 50. Therefore and preferably, the outlet valve means 47 may be formed and arranged within the outlet head 43 in a transition area adjacent to the enlargement 46 of the outlet bore 45. Thereto, the outlet head 43 may comprise a two parts structure consisting of two head halves, which may be glued with each other subsequently to the arrangement of the outlet valve means 47 within said or between said head halves. The outlet valve means 47 may comprise a simple check valve having a movably arranged valve means, such as a flap, a flag, a sail or a membrane 47, resting with at least a part of its circumferential edge section on a supporting face 48 formed at the outlet head 43 and serving as a valve seat face.

The pumping unit or pumping means 30 consisting of the hose piece 32, of the inlet head 33 and of the outlet head 43 forms an independent component which is designed as a disposable article. This component or article is formed and is intended for easy insertion into the blood pump and for easy removal from the blood pump following a single use of the pumping means, and for easy replacement by another, fresh pumping means comprising the same or a similar structure. Thereto, the inlet head 33 and the outlet head 43 may be provided with fastening means. For example, the inlet head 33 may comprise an integrally formed fastening extension 39 which may be inserted into a retaining means 11, stationarily arranged at the support means 10. In addition, the outlet head 43 may comprise an integrally formed fastening extension 49 which may be inserted into a retaining means 13 movably arranged at the support means 10, as depicted in FIG. 2. For easy distinction between the inlet head 33 and the outlet head 43 the fastening extension 39 of the inlet head 33 may comprise a specific, for example cylindric outer contour, and the stationary retaining means 11 may comprise a recess 12 having an adapted cylindric internal contour. The fastening extension 49 of the outlet head 43 may comprise another specific, for example polygonal outer contour, and the movably arranged retaining means 13 may comprise a recess 14 having an adapted polygonal internal contour.

Another kind of fastening means may comprise each a through bore 66 recessed at the inlet head 33 and a through bore 64 recessed at the outlet head 43. As depicted in FIG. 4a, said inlet head 33 may be pushed on a stationary arranged bolt 65 passing through said through bore 66, thus providing a stationary but swinging or tilting arrangement of the inlet head 33. The outlet head 43 may be pushed on a revolving peripheral link 63 passing through said through bore 64, thus providing the movable arrangement of the outlet head 43.

Further, the blood pump comprises an elongated support means 10, for example formed like a rod, a bar, a profile, a tube or the like. A retaining means 11 is arranged stationarily at one end of said support means 10. A fastening extension 39 integrally formed with the inlet head 33 may be inserted into said retaining means 11. Typically, the retaining means 11 comprises a recess 12 having an internal contour which is matched to the external contour of the fastening extension 39. Further, the support means 10 comprises additionally a movably arranged retaining means 13. A fastening extension 49 integrally formed with the outlet head 43 may be inserted into said additional retaining means 13. Typically, said additional, movably arranged retaining means 13 comprises a recess 14 having an internal contour matched to the external contour of the fastening extension 49. According to an exemplary embodiment of a driving means, said movably arranged retaining means 13 may be moved along the length direction of the elongated support means 10. Thereto, the support means 10 may comprise a groove 16 or another kind of guidance, both extending in a length direction; a foot member 15 is inserted into said groove 16 or other guidance and integrally coupled with the movably arranged retaining means 13.

Further, the blood pump according to the present invention comprises a driving means fastened to the support means 10 and enabled to move or displace the outlet head 43. According to an embodiment as depicted in FIGS. 2 and 3, said driving means comprises an electric step motor 21 arranged at a distant end of the support means 10 and driving threaded spindle 22 which engages a threaded portion or nut 23 coupled with the movably arranged foot member 15. A rotation of said threaded spindle 22 causes a displacement of the movably arranged retaining means 13 along a length direction of the support means 10. The torque and the rotational speed of the step motor 21 and the thread pitch of the spindle 22 are preferably selected and matched thus that the movably arranged retaining means 13 may perform a complete stroke consisting of a forward and backward movement within about 1 to 3 seconds. Typically, such a complete stroke may extend over a distance of about 100 mm to about 200 mm. A self-switching step motor 21 may provide both, the forward movement (in a stretching direction of the hose piece 32) and the backward movement of the movably arranged retaining means 13 under the force and control of the motor-driven spindle 22. Alternatively, the motor-driven spindle 22 may only cause the forward movement of the movably arranged retaining means 13 in order to stretch the hose piece 32. A corresponding backward movement of the retaining means 13 may be caused by a restoring force of the rubber-elastic material of the stretched hose piece 32. In this case, the electric step motor 21 may preferably and additionally comprise a regenerative electric brake ensuring in addition with the backward movement of the retaining means 13 a controlled rotational speed of the spindle 22 and thus a controlled speed of the backward movement of the retaining means 13.

Figure 4B:
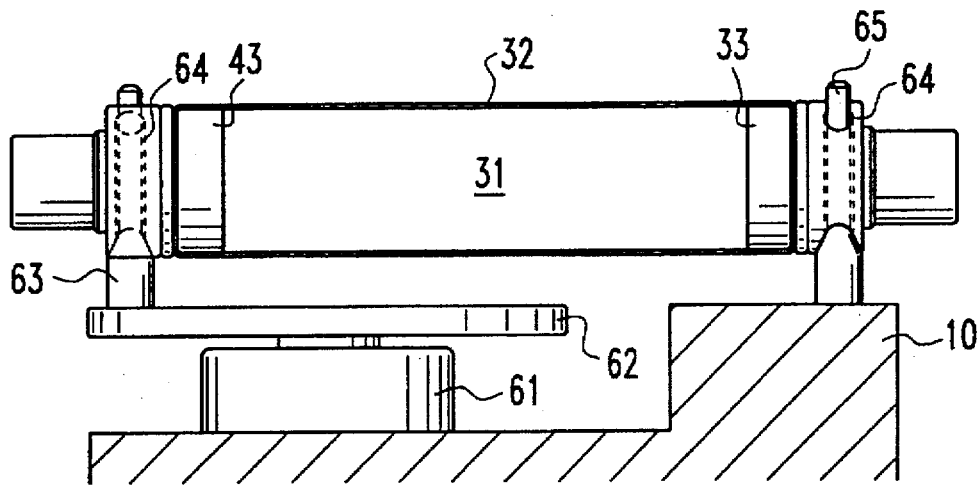
FIG. 4b shows in a similar view like FIG. 4a the hose piece in a stretched condition.

FIGS. 4a and 4b show a further exemplary embodiment of a driving means. This driving means is fastened to the support means 10 and comprises an electric motor 61 driving a rotating disc 62 having a peripheral link 63. Said peripheral link 63 may comprise a pin or bolt arranged in a peripheral section of said disc 62 and extending vertically from said disc 62. Alternatively, said peripheral link may comprise a vertically extending part of a—non-depicted—crank bolt driven by said electric motor 61. Accordingly, said peripheral link 63 is enabled to revolve along a circle path. A pumping unit comprises each an inlet head 33, a pump chamber 31 and an outlet head 43. This inlet head 33 is stationarily arranged at the support means 10, and this outlet head 43 is coupled with said peripheral link 63; for example, the outlet head 43 may comprise a through bore 64 and the peripheral link 63 is passed through said bore 64. The inlet head 33 may comprise a through bore 66 and is tiltingly arranged at a further bolt 65 stationarily arranged at the support means 10. The revolving peripheral link 63 causes a reciprocal stretching and shortening of the hose piece 32 defining the pump chamber 31. FIG. 4a shows said hose piece 32 in an essentially nonstretched condition, and FIG. 4b shows said hose piece 32 in a stretched condition.

Figure 5A:
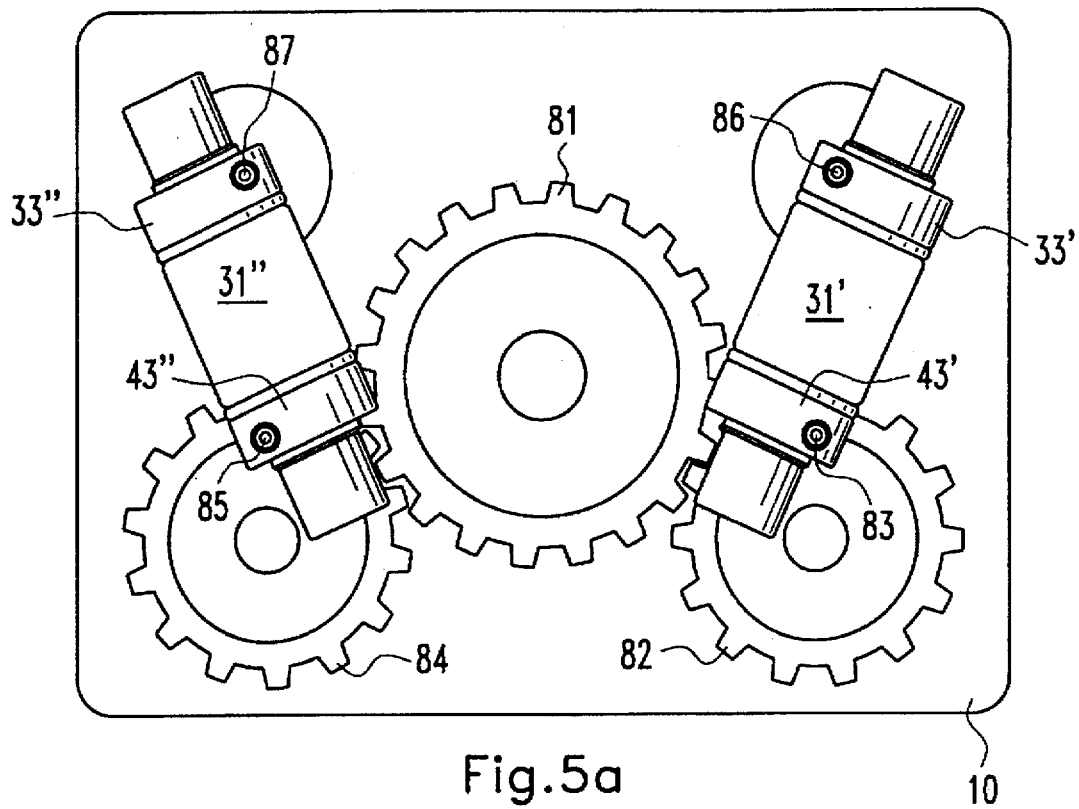
FIG. 5a shows a diagrammatic top plan view of a blood pump comprising another kind of driving means, wherein each a revolving link is vertically extending from a peripheral section of a first driven gear wheel and of a second driven gear wheel which will periodically stretch and shorten the hose piece of a first pumping means and the hose piece of a second pumping means.
Figure 5B:
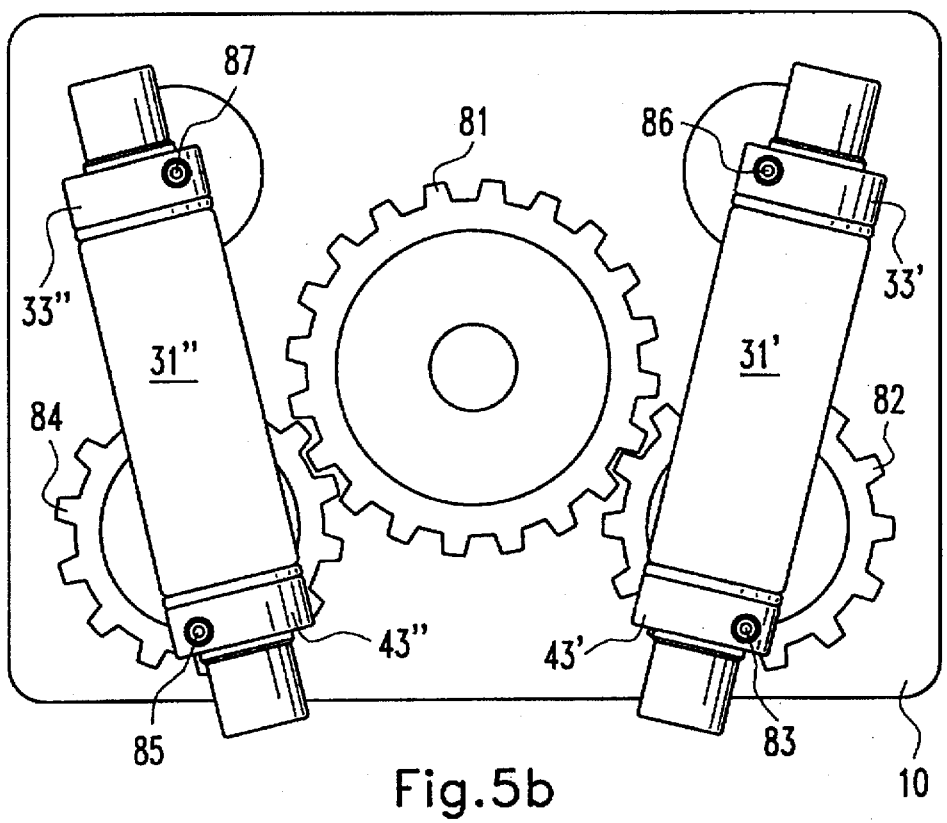
FIG. 5b shows in a similar view like FIG. 5a both hose pieces in a stretched (elongated) condition.

FIGS. 5a and 5b show a still further exemplary embodiment of a driving means. This driving means comprises a motor-driven toothed wheel 81 simultaneously driving a first gear wheel 82 and a second gear wheel 84 arranged distantly to each other and both comprising each a peripheral link 83, 85. Each of these peripheral links 83, 85 may comprise a pin or bolt arranged in a peripheral section of said gear wheels 82, 84 and vertically extending therefrom, thus enabled to revolve along a circle path whenever the toothed wheel 81 drives the gear wheels 82, 84. This type of a blood pump comprises a first pumping unit having a first inlet head 33', a first pump chamber 31' and a second outlet head 43'. Further, this blood pump comprises a second pumping unit having a second inlet head 33", a second pump chamber 31" and a second outlet head 43". Said first outlet head 33' is coupled to the peripheral link 83 of the first driven gear wheel 82, and said second outlet head 43" is coupled to the peripheral link 85 of the second driven gear wheel 84. Both, the first inlet head 33' and the second inlet head 33" are coupled independently of each other to each a bolt 86 and 87, stationarily arranged at the support means 10. Rotating the toothed wheel 81 will simultaneously operate the first pumping unit and the second pumping unit. FIG. 5a shows the first and second pump chambers 31', 31" in an essentially non-stretched condition, and FIG. 5b shows said first and second pump chambers 31', 31" in a stretched condition.

Figure 6:
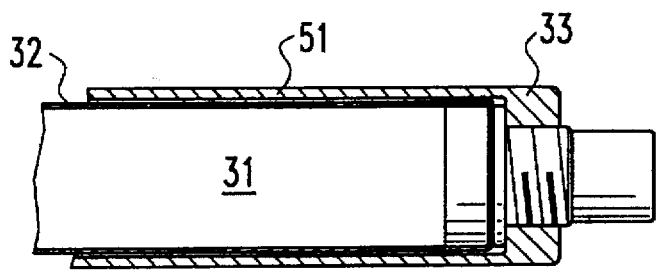
FIG. 6 shows a diagrammatic side view of a segment of a pumping means wherein an inlet head comprises an integrally formed casing in order to avoid an undue bulging of a hose piece.

In cases where the driving means causes both, an enforced stretching of the hose piece 32 and an enforced shortening of the hose piece 32, said shortening step causes at least a slight overpressure condition within the pump chamber 31 in order to pump a part of the blood into the dispensing line 50, which is contained within the pump chamber 31. This shortening or pumping step may be accompanied by an unwanted undue bulging of the hose piece 32, especially in cases of a rather thin hose piece material, such as a thin latex foil. As shown in FIG. 6, a rigid casing or envelope 51 may be provided surrounding the non-stretched hose piece 32. This envelope 51 may be integrally formed (in a one-piece manner) with the inlet head 33. An internal diameter of said rigid envelope 51 is slightly larger than an outer diameter of the non-stretched hose piece 32, thus avoiding an undue bulging during the fore-mentioned shortening or pumping step even if the hose piece 32 is made of a very thin flexible material.

As described above, the design and function of the inlet head is given by its connection to a supply line feeding blood and by the construction and function of its inlet valve means. However, and contrary to the above explanation, it is not necessary that the inlet head forms the stationarily arranged head of the pumping unit. Similarily, the design and function of the outlet head is given by its connection to a dispensing line and by the construction and function of its outlet valve means. However, and contrary to the above explanation, it is not necessary that the outlet head forms the movably arranged head of the pumping unit. Accordingly, an alternative version of a blood pump according to the present invention may comprise a movably arranged inlet head and a stationarily arranged outlet head of the pumping unit and providing the above-mentioned functions.

Besides and additionally to the fore-mentioned necessary components a blood pump according to the present invention may comprise further optionally provided components. Said optionally provided components may include sensors for sensing a blood pressure and a blood flow rate within the supply line and/or within the dispensing line. Further, said optionally provided components may include a device for introducing heparine into the fed blood, a device for sensing gas bubbles in the dispensed blood, and similar devices. Devices of said kind are known in the art and need not to be described in detail in the present specification.

The blood pump according to the present invention is suited to transport in an especially careful and gentle manner fresh natural blood through a dialyzer and/or through other means and devices of an extracorporal blood circulation system.

I claim:

1. An extra-corporal blood pump, said blood pump comprising a support means equipped with a pumping means and a driving means, wherein said pumping means comprises an inlet head, an outlet head and a pump chamber arranged between and connecting said inlet head with said outlet head, wherein:

said inlet head is stationarily arranged at said support means and comprises an inlet connector, an inlet bore having an internal diameter, and an inlet valve means;

said outlet head is movably arranged to be displaced by said driving means and comprises an outlet connector, an outlet bore having an internal diameter and an outlet valve means;

said pump chamber comprises a piece of a hose having a given original length and made of a rubber-elastic material and defining an interior volume of said pump chamber, wherein said piece of hose comprises an inlet end tightly connected with said inlet head, and further comprises a distantly arranged outlet end tightly connected with said outlet head; and said driving means periodically moving forward said outlet head essentially in a length direction of said hose piece thus stretching the hose piece in order to increase per stroke the original hose piece length by at least 100% and by not more than 500% of the original hose piece length without substantially narrowing the interior volume of the pump chamber, thus providing an enforced blood flow from the inlet bore through the pump chamber to the outlet bore.

2. The extra-corporal blood pump according to claim 1, wherein said piece of hose defines an interior volume of said pump chamber having an internal diameter not larger than five-times the internal diameter of the inlet bore or of the outlet bore or of both the inlet bore and the outlet bore.

3. The extra-corporal blood pump according to claim 2, wherein the given original length of the non-stretched hose piece is larger than the internal diameter of said non-stretched hose piece.

4. The extra-corporal blood pump according to claim 1, wherein said driving means periodically moving forward said outlet head essentially in a length direction of said hose piece thus stretching the hose piece in order to increase the original hose piece length by at least 100% and by not more than 400% of the original hose piece length.

5. The extra-corporal blood pump according to claim 1, wherein said outlet head reciprocally moving forward and backward essentially in the length direction of said hose piece, wherein said periodically moving forward being provided by said driving means; and wherein said periodically moving backward being provided by an inherent elastic restoring force of the material of the stretched hose piece.

6. The extra-corporal blood pump according to claim 1, wherein said pumping means consisting of said inlet head, said pump chamber and said outlet head is designed as a disposable article.

7. The extra-corporal blood pump according to claim 1, wherein periodically moving forward said outlet head creates a suction action within the pump chamber; said inlet valve means comprises a check valve allowing under said suction action a blood flow from a supply line connected to said inlet connector through said inlet bore into said pump chamber; and said outlet valve means comprises a check valve closing under said suction action the outlet bore.

8. The extra-corporal blood pump according to claim 1, wherein periodically moving backward said outlet head creates a pumping action within the pump chamber; said inlet valve means comprises a check valve closing under said pumping action the inlet bore; and said outlet valve means comprises a check valve allowing under said pumping action a blood flow out of the pump chamber through the outlet bore into a dispensing line connected to the outlet connector.

9. The extra-corporal blood pump according to claim 1, wherein said hose piece is made from a rubber-elastic material suited for medical purposes and selected from a group comprising silicon materials, polyurethane materials and latex materials.

10. The extra-corporal blood pump according to claim 1, wherein said blood pump comprises an elongated support means having a stationary retaining means arranged adjacent to an end portion of said support means and enabled to fasten said inlet head; and said support means further comprises a movably arranged retaining means enabled to fasten said outlet head, and guided along a groove or guidance extending in a length direction of said support means.

11. The extra-corporal blood pump according to claim 10, wherein said inlet head comprises a fastening extension insertable into said stationary retaining means; and said outlet head comprises a fastening extension insertable into said movably arranged retaining means.

12. The extra-corporal blood pump according to claim 10, wherein said driving means comprises an electric step motor driving a threaded spindle which engages a nut or a threaded portion coupled with said movably arranged retaining means.

13. The extra-corporal blood pump according to claim 12, wherein said driving means additionally comprises an electric brake means controlling a speed of the backward movement of the outlet head enforced by the inherent elastic restoring force of the hose piece material, for example said electric brake means controlling the rotational speed of the threaded spindle during the backward movement of the outlet head.

14. The extra-corporal blood pump according to claim 1, wherein said driving means comprises a motor-driven rotating disc having a peripheral link, or comprising a motor-driven crank bolt having a peripheral link, said peripheral link revolving along a circle path, said outlet head is coupled with said peripheral link; and said revolving peripheral link causes a periodical stretching and shortening of the piece of hose forming the pump chamber.

15. The extra-corporal blood pump according to claim 1, wherein said driving means comprises a motor-driven toothed wheel simultaneously driving a first gear wheel and a second gear wheel arranged distantly to each other and both comprising each a peripheral link; said blood pump comprises a first pumping means having a first inlet head, a first pump chamber and a first outlet head, and further comprises a second pumping means having a second inlet head, a second pump chamber and a second outlet head;

said first outlet head is coupled to the peripheral link of the first driven gear wheel;

said second outlet head is coupled to the peripheral link of the second driven gear wheel;

thus simultaneously operating the first pumping means and the second pumping means.

16. The extra-corporal blood pump according to claim 1, wherein said inlet head comprises a rigid envelope or casing surrounding the non-stretched hose piece and avoiding an undue bulging of said hose piece during a shortening step or pumping step of the pump chamber.

\* \* \* \* \*